United States Patent [19]

Strachan et al.

[11] 4,162,248

[45] Jul. 24, 1979

[54] SOMATOSTATIN ANALOGS

[75] Inventors: Robert G. Strachan, Warrington; William J. Paleveda, Lansdale; Daniel F. Veber, Ambler; Frederick W. Holly, Glenside, all of Pa.

[73] Assignee: Merck & Co., Inc., Rahway, N.J.

[21] Appl. No.: 894,266

[22] Filed: Apr. 7, 1978

Related U.S. Application Data

[63] Continuation-in-part of Ser. No. 781,610, Mar. 28, 1977, which is a continuation-in-part of Ser. No. 732,692, Oct. 14, 1976, abandoned.

[51] Int. Cl.$^2$ ............... A61K 37/02; C07C 103/52
[52] U.S. Cl. ........................... 260/112.5 S; 424/177
[58] Field of Search ................. 260/112.5 S; 424/177

[56] References Cited

U.S. PATENT DOCUMENTS

| | | | |
|---|---|---|---|
| 3,988,304 | 10/1976 | Garsky | 260/112.5 S |
| 4,000,259 | 12/1976 | Garsky | 260/112.5 S |
| 4,011,182 | 3/1977 | Sarantakis | 260/112.5 S |

*Primary Examiner*—Delbert R. Phillips
*Attorney, Agent, or Firm*—Walter Patton; Harry E. Westlake, Jr.

[57] ABSTRACT

Somatostatin analogs having the structural formula:

cyclo[(X)$_j$-(A)$_k$-(B)$_l$-Phe-Phe-(D- or L-)Trp-Lys-Thr-Phe-Thr-(C)$_m$]

wherein
X is

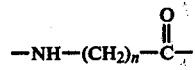

and n=0 to 4;
A is Lys, (ε-INOC) Lysine;
B is Asn, Ala, α-aminobutyric acid;
C is Ser, Gly;
j, k, l and m are 0 to 1; with the proviso that j, k, l, and m are not all 1 and not all 0, wherein the ring formed by the peptide backbone contains 24 to 33 atoms and the pharmaceutically acceptable non-toxic acid addition salts thereof are prepared by the solid phase method. These peptides have the property of inhibiting release of insulin, decreasing gastric secretion, inhibiting growth hormone release and inhibiting glucagon release in humans and animals.

12 Claims, No Drawings

SOMATOSTATIN ANALOGS

CROSS REFERENCE TO RELATED APPLICATIONS

This is a continuation-in-part application of co-pending application Ser. No. 781,610, filed Mar. 28, 1977 which is a continuation-in-part application of co-pending application Ser. No. 732,692, filed Oct. 14, 1976, now abandoned.

BACKGROUND OF THE INVENTION

Somatostatin is a tetradecapeptide having the structure:

Ala—Gly—Cys—Lys—Asn—Phe—Phe—Trp—

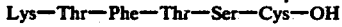
Lys—Thr—Phe—Thr—Ser—Cys—OH and is known to inhibit the release of growth hormone. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself. The present invention provides somatostatin analogs having the biological activity of somatostatin and a longer duration of action and a novel method for preparing said analogs.

The present invention further provides somatostatin analogs which are easier to prepare because they contain only 24 to 33 atoms in the peptide backbone.

SUMMARY OF THE INVENTION

This invention is concerned with novel somatostatin analogs having a longer activity than naturally occurring somatostatin and which are easier to prepare because of the smaller ring size and having the structural formula:

cyclo[(X)$_j$-(A)$_k$-(B)$_l$-Phe-Phe-(D- or L-)Trp-Lys-Thr-Phe-Thr-(C)$_m$]

wherein:
X is

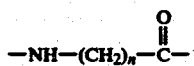

and n=0 to 4;
A is Lys, (ε-INOC) Lysine;
B is Asn, Ala, α-aminobutyric acid;
C is Ser, Gly;
j, k, l and m are 0 to 1; with the proviso that j, k, l, and m are not all 1 and not all 0,
wherein the ring formed by the peptide backbone contains 24 to 33 atoms and the pharmaceutically acceptable non-toxic acid addition salts thereof.

Illustrative of acid addition salts are hydrochloride, hydrobromide, sulfate, phosphate, maleate, acetate, citrate, benzoate, succinate, malate, ascorbate and the like.

The somatostatin analogs of the present invention differ from somatostatin by virtue of the fact that the two adjacent heteroatoms of the disulfide bridge, —S—S—, of the cystine amino acid residue of somatostatin set forth in the following structural formula:

Ala—Gly—Cys—Lys—Asn—Phe—Phe—Trp—

Lys—Thr—Phe—Thr—Ser—Cys—OH are deleted. The somatostatin analogs of the present invention include those wherein the Ala-Gly and the amino group of Cys$^3$ of somatostatin is deleted and replaced by hydrogen and the C-terminal carboxylic acid group of cystine is replaced by hydrogen. Furthermore, the somatostatin analogs of the present invention include those wherein Lys at position 4 is replaced by (ε-INOC)Lysine or deleted; Asn at position 5 is replaced by Ala, α-aminobutyric acid or deleted; Trp at position 8 is replaced by D-Trp and Ser at position 13 is replaced by Gly or deleted.

The preferred somatostatin analogs of the present invention are illustrated by the following structural formula:

cyclo[(X)$_j$-(A)$_k$-(B)$_l$-Phe-Phe-(D- or L-)Trp-Lys-Thr-Phe-Thr-(C)$_m$]

wherein
X is

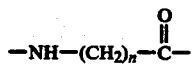

and n=0 to 4;
A is Lys;
B is Asn or α-aminobutyric acid;
C is Ser; and
j, k, l and m are 0 or 1, with the proviso that j, k, l and m are not at all 1 and not all 0,
and the pharmaceutically acceptable non-toxic acid addition salts thereof.

The structures of still further preferred somatostatin analogs are explicitly illustrated by the structural formulas:

cyclo(Lys-Asn-Phe-Phe-Trp-Lys-Thr-Phe-Thr-Ser)

cyclo(Asn-Phe-Phe-D-Trp-Lys-Thr-Phe-Thr-Ser)

cyclo(Phe-Phe-D-Trp-Lys-Thr-Phe-Thr-Ser)

cyclo(Asn-Phe-Phe-D-Trp-Lys-Thr-Phe-Thr)

and the pharmaceutically acceptable non-toxic acid addition salts thereof.

The somatostatin analogs of the present invention differ from somatostatin by virtue of the fact that they lack the N-terminal amino group and C-terminal carboxyl group thus eliminating the groups involved in enzymic cleavage of the molecule by aminopeptidases and carboxypeptidases. Furthermore, the deletion of the adjacent heteroatoms of the disulfide bridge of somatostatin increases the stability of the analogs in vivo by slowing down enzymatic degradation by reductive cleavage. Therefore, the analogs of the present invention are more resistent to cleavage in vivo than somatostatin and thus have a prolonged duration of action.

Somatostatin is a tetradecapeptide having the structure:

Ala—Gly—Cys—Lys—Asn—Phe—Phe—Trp—Lys—

Thr—Phe—Thr—Ser—Cys—OH.

The portion of somatostatin extending from amino acid Cys[3] to Cys[14] forms a dodecapeptide of the following structure:

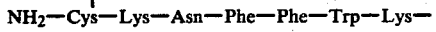

$NH_2$—Cys—Lys—Asn—Phe—Phe—Trp—Lys—

Thr—Phe—Thr—Ser—Cys—OH.

The peptide backbone and the disulfide bridge consist of a continuous 38 atom ring.

The present invention provides somatostatin analogs wherein the Ala[1]-Gly[2], the amine group of Cys[3] and carboxyl group of Cys[14] and one, two or three of the moieties (X), (A), (B) or (C), defined above are deleted, and the resulting ring contains 24 to 33 atoms.

It is a completely unexpected result that the somatostatin molecule can be modified to the extent shown in the present invention and still retain the activity of somatostatin. The present somatostatin analogs are easier to prepare because they are smaller than the parent somatostatin molecule.

The abbreviated designations, which are used herein for the amino acid components, certain preferred protecting groups, amino acid activating groups, condensing agents, reagents and solvents employed in the process of this invention are as follows:

TABLE I

| Abbreviated Designation | Amino Acid |
|---|---|
| Lys | L-lysine |
| Asn | L-asparagine |
| Phe | L-phenylalanine |
| Trp | L-tryptophan |
| D-Trp | D-tryptophan |
| Thr | L-threonine |
| Ser | L-serine |
| Asu | α-aminosuberic acid |
| Abbreviated Designation | Protecting Groups |
| INOC | isonicotinyloxycarbonyl |
| BOC | tert-butyloxycarbonyl |
| OMe | methyl ester |
| tBu | tert-butyl |
| CBZ | benzyloxycarbonyl |
| Bzl | benzyl |
| 2-Cl-CBZ | 2-chlorobenzyloxycarbonyl |
| Abbreviated Designation | Activating Groups |
| ONp | p-nitrophenyl ester |
| HSE | N-hydroxysuccinimide ester |
| HBT | 1-hydroxybenzotriazole |
| Abbreviated Designation | Condensing Agents |

TABLE I-continued

| DCCI | dicyclohexylcarbodiimide |
|---|---|
| Abbreviated Designation | Reagents |
| TFA | trifluoroacetic acid |
| TEA | triethylamine |
| DIPEA | diisopropylethylamine |
| Abbreviated Designation | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel somatostatin analogs are prepared by cyclizing the corresponding linear peptides. The linear peptides are prepared by using the solid phase sequential synthesis technique. Accordingly, the process for preparing the somatostatin analogs of the present invention comprises (a) preparing the corresponding blocked linear peptide attached to a solid phase resin; (b) selectively deblocking the N-terminal amine group; (c) removing the linear peptide from the resin; (d) treating the linear peptide with a cyclizing agent to obtain the cyclic peptide; and (e) removing the remaining blocking groups.

When the linear peptide is prepared on the resin, it is not critical which amino acid is selected to be at the C-terminal position provided only that the sequence of amino acids in the linear peptide is the same as that in the desired somatostatin analog. Once a linear peptide has been cyclized one can no longer determine which amino acid was at the C-terminus of the linear peptide. As an example to illustrate this, either of the two following linear peptides, when cyclized, will give the identical somatostatin analog:

D—Trp-(ε-INOC)Lys—O—Bzl—Thr—Phe—O—
Bzl—Thr—Asn—Phe—Phe—$N_3$
  or
Asn—Phe—Phe—D—Trp-(ε-INOC)Lys—O—
Bzl—Thr—Phe—O—Bzl—Thr—$N_3$

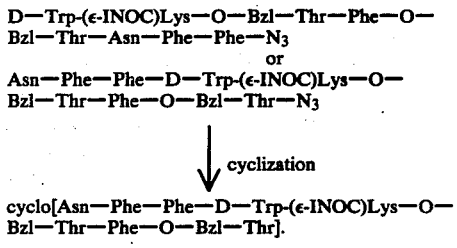

cyclization cyclo[Asn—Phe—Phe—D—Trp-(ε-INOC)Lys—O—
Bzl—Thr—Phe—O—Bzl—Thr].

It is evident that since the linear peptide is going to be cyclized, it does not matter which amino acid is used to start the chain. Starting with Phe at the carboxyl end, as illustrated in the first of the two examples above, has several advantages over the second example. In the first example, D-Trp, which is susceptible to oxidative degradation, is the N-terminal amino acid and thus will be added last and hence will be subjected to the least amount of exposure to oxidative degradation. Also, all deblocking steps prior to the addition of D-Trp will not require the presence of a scavenger (such as ethanedithiol).

The synthesis of the linear peptides by the solid phase technique is conducted in a stepwise manner on chloromethylated resin. The resin is composed of fine beads (20–70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin. The chlorine is benzyl chloride is attached by a reactive type of linkage.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e., trifluoro acetic acid, or hydrogen chloride or ethyl acetate).

The —OH group of Thr can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups. This selectivity in removing protecting groups is illustrated by reference to Tables II and III.

After the linear peptide has been formed on the solid phase resin, it may be removed by a variety of methods which are well known in the art. For example, the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear hexapeptide. In the case wherein the ester is the methyl ester, the resulting compound may be converted to the azide via the hydrazide which may then be cyclized to the desired cyclic peptide. The preferred method in the present invention is the use of hydrazine.

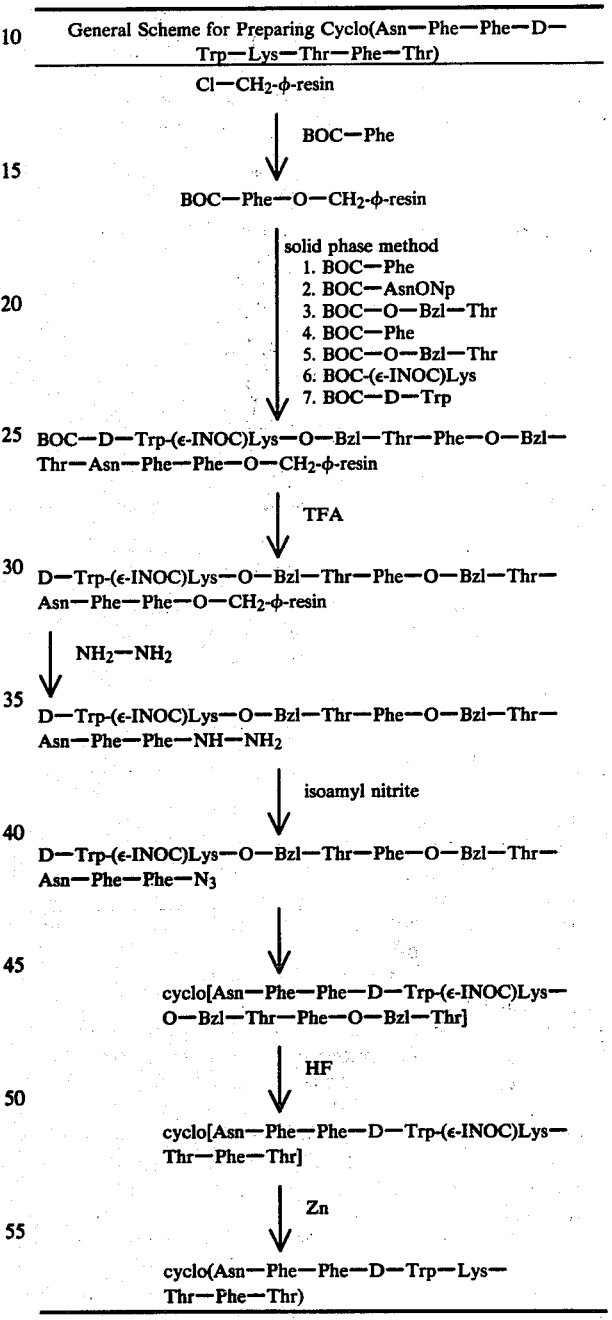

TABLE II — General Scheme for Preparing Cyclo(Asn—Phe—Phe—D—Trp—Lys—Thr—Phe—Thr)

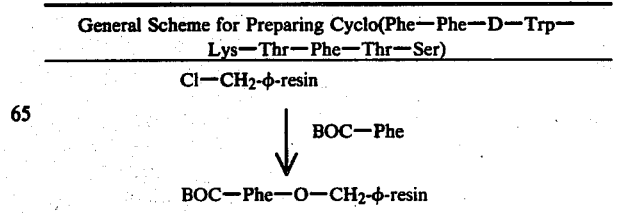

TABLE III — General Scheme for Preparing Cyclo(Phe—Phe—D—Trp—Lys—Thr—Phe—Thr—Ser)

TABLE III-continued

General Scheme for Preparing Cyclo(Phe—Phe—D—Trp—Lys—Thr—Phe—Thr—Ser)

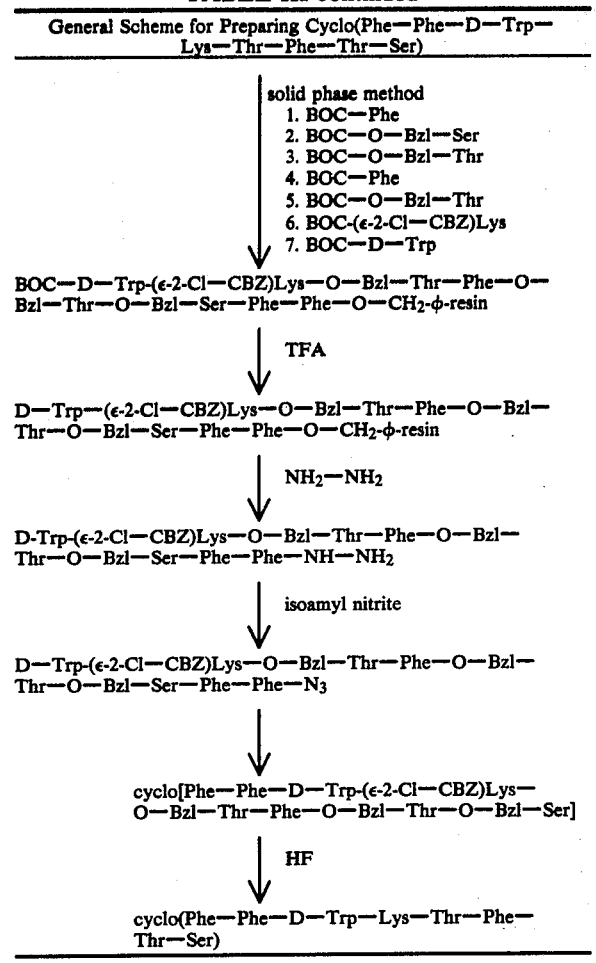

As reference to Tables II and III will show, one preferred overall procedure for preparing the desired cyclic peptides of the present invention involves the stepwise synthesis of the linear peptide on a solid phase resin. More specifically, in the process for preparing cyclo(Asn-Phe-Phe-D-Trp-Lys-Thr-Phe-Thr), the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence: D-Trp-(ε-INOC)Lys-O-Bzl-Thr-Phe-O-Bzl-Thr-Asn-Phe-Phe-NH-$NH_2$ is treated with isoamyl nitrite in acid pH to form the corresponding azide. The azide solution is diluted with solvent and neutralized with an organic base. The linear peptide cyclizes to form cyclo[D-Trp-(ε-INOC)Lys-O-Bzl-Thr-Phe-O-Bzl-Thr-Asn-Phe-Phe]. During the cyclization the "ph" is checked and maintained at neutral by the addition of organic base. The "pH" in organic solvent is determined by the application of an aliquot of the solution to moist narrow range pH paper.

After the linear peptide is cyclized, the remaining protective groups are removed. The Bzl groups are removed by treatment with HF in the presence of anisole and the INOC groups are removed with activated zinc in acetic acid to obtain the desired cyclic peptide cyclo(D-Trp-Lys-Thr-Phe-Thr-Asn-Phe-Phe).

As reference to Table III shows, the protective groups 2-Cl-CBZ abd Bzl are removed in one step by treatment with HF in the presence of anisole. The crude cyclic peptides obtained by the processes of Tables II and III are purified by chromatography, preferably on Sephadex eluted with 50% aqueous acetic acid.

The following Examples illustrate methods of carrying out the present invention, but is to be understood that these Examples are given fior purposes of illustration and not of limitation.

EXAMPLE 1

Preparation of Cyclo(Asn-Phe-Phe-D-Trp-Lys-Thr-Phe-Thr)

Step (a) — Preparation of D-Trp-(ε-INOC)Lys-O-Bzl-Thr-Phe-D-Bzl-Thr-Asn-Phe-Phe-O-$CH_2$-φ-Resin Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3×2000 ml. of tetrahydrofuran
4×5170 ml. of ethanol
1×5170 ml. of acetic acid
3×5170 ml. of water
3×5170 ml. of methanol
3×5170 ml. of chloroform.

The BOC-Phe-O-$CH_2$-φ-resin was dried in vacuo at 25° C. for 16 hours, giving 1203 g. of BOC-Phe-O-$CH_2$-φ-resin containing 0.937 mmole of phenylalanine/g. of resin.

BOC-Phe-O-$CH_2$-φ-resin (4.69 g.; 4.0 mmole) was carried through the procedures in Table IV and V using 2 deblockings (2 minutes and 25 minutes) with 25% TFA in methylene chloride, and 2.5 equivalents of BOC-amino acid in the required sequence until the desired BOC-octapeptide-O-$CH_2$-φ-resin was obtained.

DCCI was used as the coupling agent in every step except the coupling of BOC-Asn to Phe-Phe-O-$CH_2$-φ-resin in which case the p-nitrophenyl ester of BOC-Asn, (BOC-Asn-ONp), was used.

The coupling of each amino acid proceeded smoothly with one coupling reaction in every step except in the two steps, coupling of BOC-AsnONp to Phe-Phe-O-$CH_2$-φ-resin and the coupling of BOC-O-Bzl-Thr to Asn-Phe-Phe-O-$Ch_2$-φ-resin. Both of these steps required a repetition of the coupling reaction to obtain best results. Of course, the coupling step is repeated without going through the deblocking step.

The coupling reactions were carried out in methylene chloride, DMF or a mixture of these two solvents. The N-terminal amino group was blocked with a BOC group in each case; the hydroxy group of Thr was blocked with Bzl and the ε-amino group of Lys with INOC.

The sequence of coupling steps and the solvent used is set forth in Table V.

When the desired BOC-octapeptide-O-CH$_2$-φ-resin was obtained, the N-terminal BOC group was removed by the terminal deblocking procedure set forth in Table VI.

Step (b) — Preparation of D-Trp-(ε-INOC)-Lys-O-Bzl-Thr-Phe-O-Bzl-Thr-Asn-Phe-Phe-NH-NH$_2$ To a mixture of 2.001 g. D-Trp-(ε-INOC)-Lys-O-Bzl-Thr-Phe-O-Bzl-Thr-Asn-Phe-Phe-O-CH$_2$-φ-resin (containing 0.43 mmole peptide per g. equivalent to 0.86 g. peptide) in 20 ml. freshly degassed DMF was added 2 ml. NH$_2$-NH$_2$. The mixture was magnetically stirred at room temperature for 1 hour. The mixture was filtered to remove the resin. The resin was washed with 4×5 ml. DMF. The filtrate and washings were concentrated

TABLE IV

| Solvent or reagent (number of washes) | CHCl$_3$ (2) | 25% TFA in CH$_2$Cl$_2$ (2) | CHCl$_3$ (3) | NEt$_3$-CH$_2$Cl$_2$ (1:9) (2) | CHCl$_3$ (3) CH$_2$Cl$_2$ (3) * | BOC AA in CH$_2$Cl$_2$, DMF or a mixture of both | 0.5M PCCI in CH$_2$Cl$_2$ ** | CH$_2$Cl$_2$ (1) MeOH (1) DMF (1) MeOH (1) CHCl$_2$ (2)* |
|---|---|---|---|---|---|---|---|---|
| Volume ml. | 60 | 60 | 60 | 60 | 60 | 60 ml. | 20 | 60 |
| Time/min. | 5 | 2 and 25 | 2 | 5 and 5 | 2 | 5 | 5 min. coupling 120 min. | 2 |

*When BOC Active Ester Coupling is employed: 3 DMF washes are employed instead.
**When BOC Active Ester Coupling is employed: No DCCI addition and coupling time is 600 min.

TABLE V

| Protected Amino Acid | Solvent ml. |
|---|---|
| BOC-Phe | CH$_2$Cl$_2$, 50 ml. |
| BOC-AsnONp | DMF, 50 ml. |
| recouple | DMF, 50 ml. |
| BOC-O-Bzl-Thr | CH$_2$Cl$_2$, 50 ml. |
| recouple | CH$_2$Cl$_2$, 50 ml. |
| BOC-Phe | CH$_2$Cl$_2$, 50 ml. |
| BOC-O-Bzl-Thr | CH$_2$Cl$_2$, 50 ml. |
| BOC-(ε-INOC)Lys | DMF, 22 ml. and CH$_2$Cl$_2$, 28 ml. |
| BOC-D-Trp | DMF, 11 ml. and CH$_2$Cl$_2$, 39 ml. |

TABLE VI

TERMINAL DEBLOCKING PROGRAM

| | CHCl$_3$(1) | 25% TFA in CH$_2$Cl$_2$ + 1% Ethanedithiol (2) | CHCl$_3$ (3) | MeOH (2) CH$_2$Cl$_2$ (1) MeOH (2) CH$_2$Cl$_2$ (2) |
|---|---|---|---|---|
| Vol./ml. | 60 | 60 | 60 | 60 |
| Time in minutes | 5 | 2 and 25 | 2 min. | 2 min. |

After terminal deblocking the octapeptide-O-CH$_2$-φ-resin was filtered and dried overnight in vacuo. It weighed 9.72 grams. By Spinco amino acid analysis, it contained 0.43 mmole of peptide per gm. Amino acid analysis after hydrolysis for 4 hours in HCl/propionic acid yielded the following results:

| | μmole/mg. | normalized to phenylalanine |
|---|---|---|
| Lys | 0.404 | 0.94 |
| NH$_3$ | 0.712 | 1.66 |
| Asp | 0.439 | 1.02 |
| Thr | 0.625 | 1.45 |
| Phe | 1.29 | 3.00 | in vacuo to a small volume. An excess of water is added to precipitate the solids. The solids were collected by filtration, washed several times with small volumes of water until all traces of formyl hydrazide are removed. The solid is dried in vacuo overnight to give 1.1621 g. of solids.

The solids were dissolved in 25 ml. freshly degassed DMF and the solution concentrated to near dryness. To the concentrated solution was added 30 ml. 95% ethanol to obtain a gelatinous solid. The solid was collected by filtration and washed with 2×10 ml. ethanol and 2×10 ml. peroxide free ether. The resulting solid was dried in vacuo overnight to yield 0.90 g. of product.

Step (c) — Preparation of D-Trp-(ε-INOC)-Lys-O-Bzl-Thr-Phe-O-Bzl-Thr-Asn-Phe-Phe-N$_3$ D-Trp-(ε-INOC)Lys-O-Bzl-Thr-Phe-O-Bzl-Thr-Asn-Phe-Phe-NH-NH$_2$ (887.7 mg., 0.625 mmole), prepared by the process set forth in Step (b), is suspended in 9 ml. freshly degassed DMF. The turbid solution is stirred magnetically at −25° C. under a nitrogen atmosphere. To the suspension is added 0.51 ml., 6.3 N HCl in THF (-INOC)Lys-Thr-Phe-Thr]mmole, 5.12 equivalents). To the resulting clear acidic solution, "pH" 1.5 to 2.0, is added 100λ isoamyl nitrite (0.75 mmole, 1.2 equivalents) and stirring continued for 40 minutes. This solution of D-Trp-(ε-INOC)Lys-O-Bzl-Thr-Phe-O-Bzl-Thr-Asn-Phe-Phe-N$_3$ is used immediately in Step d).

Step (d) - Preparation of Cyclo[Asn-Phe-Phe-D-Trp-(ε-INOC)Lys-O-Bzl-Thr-Phe-O-Bzl-Thr]

The solution of D-Trp-(ε-INOC)Lys-O-Bzl-Thr-Phe-O-Bzl-Thr-Asn-Phe-Phe-N$_3$ in DMF, obtained by the process set forth in Step c), is diluted in 880 ml. freshly degassed DMF, precooled to −50° C. The solution is maintained under a nitrogen atmosphere and allowed to warm to −20° C. during which time the "pH" was maintained at 7.2 to 7.6 by the addition of N,N-diisopropylethylamine. The solution was maintained at −16° C. for 24 hours and then kept at 5° C. for an additional 18 hours. During this period the "pH" is checked. N,N-Di-isopropyl ethylamine is added in sufficient amount to maintain a "pH" of 7.2 to 7.6.

The solution was concentrated in vacuo to a thick oil and triturated with 50 ml. water to give a solid. The solid was collected by filtration, slurried with 4×10 ml. water, filtered and dried in vacuo overnight to give 0.85 g. of product. Yield 98%.

Step (e) —Preparation of
Cyclo[Asn-Phe-Phe-D-Trp-(ε-INOC)
Lys-Thr-Phe-Thr)

Cyclo[Asn-Phe-Phe-D-Trp-(ε-INOC)Lys-O-Bzl-Thr-Phe-O-Bzl-Thr], 758.7 mg. (0.547 mmole), obtained by the process set forth in Step (d), was dissolved in 2 ml. anisole and 20 ml. hydrogen fluoride at ice-bath temperature. The solution was stirred magnetically at ice-bath temperature for 1 hour. The excess hydrogen fluoride was removed in vacuo at ice-bath temperature. The resulting oily residue was maintained in vacuo for an additional hour at ice-bath temperature and triturated with 35 ml. ethyl acetate to give a solid. The solid was collected by centrifugation, washed with 3×35 ml. ethyl acetate and dried in vacuo to give 604.2 mg. (91.5% yield) of product.

Step (f) 13 Preparation of
cyclo(Asn-Phe-Phe-D-Trp-Lys-Thr-Phe-Thr)

Cyclo[Asn-Phe-Phe-D-Trp(ε-INOC)Lys-Thr-Phe-Thr], 554.7 mg. (0.46 mmole), obtained by the process set forth in Step (e), was dissolved in 5.6 ml. 50% aqueous acetic acid. Activated zinc, 0.56 g., was added and the mixture stirred vigorously at room temperature for 5 hours. An additional 5.6 ml. of 50% aqueous acetic acid and 0.56 g. activated zinc was added and the mixture stirred at room temperature overnight. The excess zinc was removed by filtration and the zinc washed with 2×2 ml. 50% aqueous acetic acid. The filtrate and washings containing the product were combined and subjected to chromatography on Sephadex G-25 as set forth in Step (g).

Step (g) — Purification of
Cyclo(Asn-Phe-Phe-D-Trp-Lys-Thr-Phe-Thr)

The aqueous acetic acid filtrate and washings obtained in Step (f) were charged to a column of Sephadex G-25, super fine, (5 cm. × 115 cm., 2260 ml.) packed in 50% aqueous acetic acid. The column was eluted with 50% aqueous acetic acid and 18.7 ml. fractions were collected.

Fractions 71 and 73 to 79 were combined, concentrated to dryness in vacuo and the residue lyophilized from 20 ml. 10% aqueous acetic acid to give 305.7 mg. of substantially pure product. A 20 hour acid hydrolysate showed the following amino acid analysis:

| | μmole/mg. | normalized to phenylalanine |
|---|---|---|
| Lys | 0.776 | 1.01 |
| $NH_3$ | 0.91 | 1.19 |
| Asp | 0.786 | 1.03 |
| Thr | 1.59 | 2.07 |
| Phe | 2.30 | 3.00 |

Fraction 72 was concentrated in vacuo to dryness and lyophilized from 10 ml. 10% aqueous acetic acid to give 22.4 mg. product. A 20 hour acid hydrolysate showed the following amino acid analysis:

| | μmole/mg. | normalized to phenylalanine |
|---|---|---|
| Lys | 0.844 | 1.01 |
| $NH_3$ | 1.14 | 1.36 |
| Asp | 0.815 | 0.97 |
| Thr | 1.72 | 2.06 |
| Phe | 2.51 | 3.00 |

EXAMPLE 2

Preparation of
Cyclo(Phe-Phe-D-Trp-Lys-Thr-Phe-Thr-Ser)

Step (a) — Preparation of
D-Trp-(ε-2-Cl-CBZ)Lys-D-Bzl-Thr-Phe-O-Bzl-Thr-D-Bzl-Ser-Phe-Phe-D-Ch-hd 2-φ-Resin BOC-Phe-O-$CH_2$-φ-resin, prepared by the process set forth in Example 1, Step (a), (4.69 g.; 4.0 mmole) was carried through the procedures in Table VII and VIII using 2 deblockings (2 minutes and 25 minutes) with 25% TFA in methylene chloride, and 2.5 equivalents of BOC-amino acid in the required sequence until the desired BOC-octapeptide-O-$CH_2$-φ-resin was obtained.

DCCI was used as the coupling agent in every step.

The coupling of each amino acid proceeded smoothly with one coupling reaction in every step except in the two steps, coupling of (ε-2-Cl-CBZ) Lys to O-Bzl-Thr-Phe-O-Bzl-Thr-O-Bzl-Ser-Phe-Phe-O-$CH_2$-φ-resin and the coupling of BOC-D-Trp to (ε-2-Cl-CBZ)Lys-O-Bzl-Thr-Phe-O-Bzl-Thr-O-Bzl-Ser-Phe-Phe-O-$Ch_2$-φ-resin. Both of these steps required a repetition of the coupling reaction to obtained best results.

The coupling reactions were carried out in methylene chloride, or a mixture of DMF and methylene chloride. The N-terminal amino group was blocked with a BOC group in each case; the hydroxy group of Ser and Thr was blocked with Bzl and the ε-amino group of Lys with 2-chlorbenzyloxy-carbonyl, (2-Cl-CBZ).

The sequence of coupling steps and the solvent used is set forth in Table VIII.

When the desired BOC-octapeptide-O-$CH_2$-φ-resin was obtained, the N-terminal BOC group was removed by the terminal deblocking procedure set forth in Table IX.

TABLE VII

| Solvent or reagent (number of washes) | $CHCl_3$ (2) | 25% TFA in $CH_2Cl_2$ (2) | $CHCl_3$ (3) | $NEt_3$ $CH_2Cl_2$ (1:9) (2) | $CHCl_3$ (3) $CH_2Cl_2$ (3) | BOC AA in $CH_2Cl_2$, DMF or a mixture of both | 0.5M DCCI in $CH_2Cl_2$ | $CH_2Cl_2$ (1) MeOH (1) DMF (1) MeOH (1) $CHCl_3$ (2) |
|---|---|---|---|---|---|---|---|---|
| Volume ml. | 60 | 60 | 60 | 60 | 60 | 50 ml. | 20 | 60 |
| Time/min. | 2 | 2 and 25 | 2 | 5 and 5 | 2 | 5 | 5 min. coup- | 2 |

TABLE VII-continued

| Solvent or reagent (number of washes) | 25% TFA in CHCl₃ (2) | 25% TFA in CH₂Cl₂ (2) | CHCl₃ (3) | NEt₃-CH₂Cl₂ (1:9) (2) | CHCl₃ (3) CH₂Cl₂ (3) | BOC AA in CH₂Cl₂, DMF or a mixture of both | 0.5M DCCI in CH₂Cl₂ | CH₂Cl₂ (1) MeOH (1) DMF (1) MeOH (1) CHCl₃ (2) |
|---|---|---|---|---|---|---|---|---|
| | | | | | | | ling 120 min. | |

TABLE VIII

| Protected Amino Acid | Solvent ml. |
|---|---|
| BOC-Phe | CH₂Cl₂, 50 ml. |
| BOC-O-Bzl-Ser | CH₂Cl₂, 50 ml. |
| BOC-O-Bzl-Thr | CH₂Cl₂, 50 ml. |
| BOC-Phe | CH₂Cl₂, 50 ml. |
| BOC-O-Bzl-Thr | CH₂Cl₂, 50 ml. |
| BOC-(ε-2-Cl-CBZ)Lys | CH₂Cl₂, 50 ml. |
| recouple | CH₂Cl₂, 50 ml. |
| BOC-D-Trp | DMF, 11 ml. and CH₂Cl₂, 39 ml. |
| recouple | DMF, 11 ml. and CH₂Cl₂, 39 ml. |

TABLE IX
TERMINAL DEBLOCKING PROGRAM

| | CHCl₃ (1) | 25% TFA in CH₂Cl + 1% Ethanedithiol (2) | CHCl₃ (3) | MeOH (2) CH₂Cl₂ (1) MeOH (2) CH₂Cl₂ (2) |
|---|---|---|---|---|
| Vol./ml. | 60 | 60 | 60 | 60 |
| Time in minutes | 5 | 2 and 25 | 2 min. | 2 min. |

After terminal deblocking the octapeptide-O-CH₂-φ-resin was filtered and dried overnight in vacuo. It weighed 9.52 grams. By Spinco amino acid analysis, it contained 0.43 mmole of peptide per gram. Amino acid analysis after hydrolysis for 4 hours in HCl/propionic acid yielded the following results:

| | μmole/mg. | normalized to phenylalanine |
|---|---|---|
| Lys | 0.410 | 0.95 |
| NH₃ | 0.369 | 0.86 |
| Asp | 0.016 | 0.04 |
| Thr | 0.710 | 1.65 |
| Ser | 0.219 | 0.51 |
| Phe | 1.29 | 3.00 |

Step (b)—Preparation of D-Trp-(ε-2-Cl-CBZ)Lys-O-Bzl-Thr-Phe-O-Bzl-Thr-O-Bzl-Ser-Phe-Phe-NH-NH₂

To a mixture of 4.0 g. D-Trp-(ε-2-Cl-CBZ)Lys-O-Bzl-Thr-Phe-O-Bzl-Thr-O-Bzl-Ser-Phe-Phe-O-CH₂-φ-resin (containing 0.43 mmole peptide per g.) in 40 ml. freshly degassed DMF was added 4 ml. NH₂-NH₂. The mixture was magnetically stirred at room temperature for 1 hour. The mixture was filtered to remove the resin. The resin was washed with 4×10 ml. DMF. The filtrate and washings were concentrated in vacuo to near dryness. The semi-solid residue was triturated with 50 ml. water to obtain a solid. The solid was collected by filtration, washed with water 4 × 30 ml. or until all the formylhydrazide has been removed and dried in vacuo overnight to give 2.07 g. of solids.

Step (c)—Preparation of D-Trp-(ε-2-Cl-CBZ(Lys-O-Bzl-Thr-Phe-O-Bzl-Thor-O-Bzl-Ser-Phe-Phe-N₃

D-Trp(ε-2-Cl-CBZ)Lys-O-Bzl-Thr-Phe-O-Bzl-Thr-O-Bzl-Ser-Phe-Phe-NH-NH₂ (1.0047 g., 0.66 mmole), prepared by the process set forth in Step (b), was suspended in 10 ml. freshly degassed DMF. The turbid solution was stirred magnetically at −25° C. under a nitrogen atmosphere. To the suspension was added 0.52 ml. 6.3 N HCl in THF (3.3 mmole, 5.00 equivalents). To the resulting clear acidic solution, "pH" 1.5, was added 110 λ isoamyl nitrite (0.82 mmole, 1.25 equivalents) and stirred continuously for 2 hours. This solution of D-Trp-(ε-2-Cl-CBZ)Lys-O-Bzl-Thr-Phe-O-Bzl-Thr-O-Bzl-Ser-Phe-Phe-N₃ was used immediately in Step (d).

Step (d)—Preparation of Cyclo[Phe-Phe-D-Trp-(ε-2-Cl-CBZ)Lys-O-Bzl-Thr-Phe-O-Bzl-Thr-O-Bzl-Ser]

The solution of D-Trp-(ε-2-Cl-CBZ)Lys-O-Bzl-Thr-Phe-O-Bzl-Thr-O-Bzl-Ser-Phe-Phe-N₃ in DMF, obtained by the process set forth in Step (c), was diluted in 990 ml. freshly degassed DMF, precooled to −50° C. The solution was maintained under a nitrogen atmosphere and allowed to warm to −20° C. during which time the "pH" was maintained at 7.2 to 7.6 by the addition of N,N-diisopropylethylamine. The solution was maintained at −16° C. for 24 hours. The solution was stored at 4° C. for 3 days. The "pH" was checked and maintained at 7.2 to 7.6 by addition of N,N-diisopropylethylamine.

The solution was concentrated in vacuo to a thick oil and triturated with 50 ml. water to give a solid. The solid was collected by filtration, slurried with 4 × 10 ml. water, filtered and dried in vacuo overnight to give 0.97 g. of product.

Step (e)—Preparation of Cyclo(Phe-Phe-D-Trp-Lys-Thr-Phe-Thr-Ser)

Cyclo[Phe-Phe-D-Trp(ε-2-Cl-CBZ)Lys-O-Bzl-Thr-Phe-O-Bzl-Thr-O-Bzl-Ser], 700.7 mg. (0.472 mmole), obtained by the process set forth in Step (d), was dissolved in 2 ml. anisole and 20 ml. hydrogen fluoride at ice-bath temperature. The solution was stirred magnetically at ice-bath temperature for 1 hour. The excess hydrogen fluoride was removed in vacuo at ice-bath temperature. The resulting oily residue was maintained in vacuo for an additional hour at ice-bath temperature and triturated with 50 ml. ethyl acetate to give a solid. The solid was collected by filtration, washed several times with ethyl acetate and dried in vacuo to give 0.52 g. (105.5% yield) of product.

Step (f) Purification of Cyclo(Phe-Phe-D-Trp-Lys-Thr-Phe-Thr-Ser)

Cyclo (Phe-Phe-D-Trp-Lys-Thr-Phe-Thr-Ser), obtained by the process set forth in Step (e), 478.5 mg. was dissolved in 5 ml. 50% aqueous acetic acid. To this solution was added 0.25 g. sucrose to make the solution dense and the solution layered under the eluant of a column of Sephadex G-25, super fine, (5 cm. × 115 cm., 2260 ml.) packed in 50% aqueous acetic acid. The column was eluted with 50% aqueous acetic acid and 18.7 ml. fractions were collected.

Fractions 71 to 77 and 79 to 84 were combined, concentrated to drynes in vacuo and the residue lyophilized from 15 ml. water to give 236.0 mg. of substantially pure product. A 20 hour acid hydrolysate showed the following amino acid analysis:

|  | μmole/mg. | normalized to phenylalanine |
|---|---|---|
| Lys | 0.801 | 0.99 |
| NH$_3$ | 0.37 | 0.46 |
| Thr | 1.60 | 1.98 |
| Ser | 0.809 | 1.00 |
| Phe | 2.42 | 3.00 |

Fractions 72 was concentrated in vacuo to dryness and lyophilized from 5 ml. water to give 23.0 mg. product. A 20 hour acid hydrolysate showed the following amino acid analysis:

|  | μmole/mg. | normalized to phenylalanine |
|---|---|---|
| Lys | 0.813 | 0.99 |
| NH$_3$ | 0.324 | 0.39 |
| Thr | 1.66 | 2.02 |
| Ser | 0.806 | 0.98 |
| Phe | 2.47 | 3.00 |

The somatostatin analogs of the present invention are useful in humans and animals for inhibiting gastric secretion in the treatment of gastric ulcers, inhibiting growth hormone release as in the treatment of acromegaly, inhibiting the release of glucagon and alone or in conjunction with insulin, for lowering blood glucose as in the treatment of diabetes. In the treatment of diabetes, the number and size of daily doses and the time of administration are determined by an individual study of each subject. The method of determing these factors is known to those skilled in the art.

The somatostatin analogs described herein may be administered to warm blooded animals, including humans, either intravenously, subcutaneously, intramuscularly or orally. The contemplated dose range for oral administration in tablet or capsule form to large mammals is about 0.001 mg. to about 7 mg/k. of body weight per day. These somatostatin analogs are preferably administered by injection. A therapeutically effective amount of an analog is oridinarily supplied at a dosage level of from about 0.001 mg. to about 2 mg./kg. of body weight. Preferably the range is from about 0.00142 mg. to about 0.428 mg./kg. of body weight administered by intravenous infusion or by subcutaneous injection. The required dosage will vary with the particular condition being treated, the severity of the condition and the duration of treatment.

If the active ingredient is administered in tablet form, the tablet may contain; a binder such as gum tragacanth, corn starch, gelatin, an excipient such as dicalcium phosphate; a disintegrating agent such as corn starch, and alginic acid; a lubricant such as magnesium stearate; and a sweetening and/or flavoring agent such as surcrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of cyclo(Asn-Phe-Phe-D-Trp-Lys-Thr-Phe-Thr) suitable for subcutaneous injection.

EXAMPLE 3

1 ml. sterile saline;

1 mg. cyclo(Asn-Phe-Phe-D-Trp-Lys-Thr-Phe-Thr).

What is claimed is:

1. Compounds of the formula:

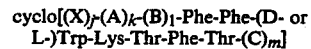

wherein
X is

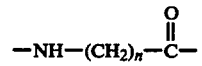

and n=0 to 4;

A is Lys, ε-INOC-Lysine;

B is Asn, Ala, α-aminobutyric acid;

C is Ser, Gly; j, k, l and m are 0 or 1, with the proviso that j, k, l, and m are not all 1 and not all 0; wherein the ring formed by the peptide backbone contains 24 to 33 atoms and pharmaceutically acceptable non-toxic acid addition salts thereof.

2. The compound according to claim 1 wherein X is

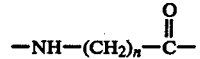

and n=0 to 4;

A is Lys;

B is Asn or α-aminobutyric acid;

C is Ser; j, k, l and m are 0 or 1, with the proviso that j, k, l, and m are not all 1 and not all 0.

3. The compound according to claim 2 wherein j is zero.

4. The compound according to claim 3 wherein k is zero.

5. The compound according to claim 4 wherein l is zero.

6. The compound according to claim 4 wherein m is zero.

7. The compound according to claim 3 having the formula:

8. The compound according to claim 4 having the formula:

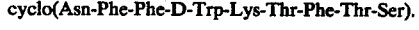

9. The compound according to claim 5 having the formula:

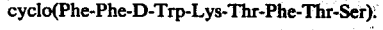

10. The compound according to claim 6 having the formula:

cyclo(Asn-Phe-Phe-D-Trp-Lys-Thr-Phe-Thr).

11. A composition comprising a therapeutically effective amount of the peptides having the structure:

cyclo[(X)$_j$-(A)$_k$-(B)$_l$-Phe-Phe-(D-or L-)Trp-Lys-Phe-Thr-(C)$_m$]

wherein
X is

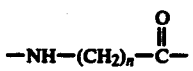

and n=0 to 4;
A is Lys, ε-INOC-Lysine;
B is Asn, Ala, α-aminobutyric acid;
C is Ser, Gly; j, k, l and m are 0 or 1, with the provisio that j, k, l and m are not all 1 and not all 0; and pharmaceutically acceptable non-toxic acid addition salts thereof and a pharmaceutically acceptable carrier.

12. A composition comprising a therapeutically effective amount of the peptides having the structure:

cyclo[(X)$_j$-(A)$_k$-(B)$_l$-Phe-Phe-(D- or L-)Trp-Lys-Thr-Phe-Thr-(C)$_m$]

wherein
X is

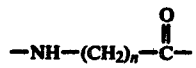

and n=0 to 4;
A is Lys;
B is Asn or α-aminobutyric acid;
C is Ser; j, k, l and m are 0 or 1, with the proviso that j, k, l and m are not all 1 and not all 0; and pharmaceutically acceptable non-toxic acid addition salts thereof and a pharmaceutically acceptable carrier.

* * * * *